(12) United States Patent
Willmann et al.

(10) Patent No.: US 9,095,653 B2
(45) Date of Patent: *Aug. 4, 2015

(54) METHOD FOR THE TIMED DOSAGE OF MEDICAMENTS

(75) Inventors: Stefan Willmann, Düsseldorf (DE); Walter Schmitt, Neuss (DE); Jörg Lippert, Leverkusen (DE); Ingmar Dorn, Köln (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 1442 days.

This patent is subject to a terminal disclaimer.

(21) Appl. No.: 10/598,416

(22) PCT Filed: Feb. 19, 2005

(86) PCT No.: PCT/EP2005/001745
§ 371 (c)(1),
(2), (4) Date: Oct. 6, 2006

(87) PCT Pub. No.: WO2005/084731
PCT Pub. Date: Sep. 15, 2005

(65) Prior Publication Data
US 2007/0196479 A1 Aug. 23, 2007

(30) Foreign Application Priority Data
Mar. 4, 2004 (DE) .......................... 10 2004 010 516

(51) Int. Cl.
| G06F 7/60 | (2006.01) |
| G06F 17/50 | (2006.01) |
| G06F 19/00 | (2011.01) |
| G01N 33/48 | (2006.01) |

(Continued)

(52) U.S. Cl.
CPC ............. *A61M 5/1723* (2013.01); *G06F 19/12* (2013.01); *G06F 19/26* (2013.01); *G06F 19/3437* (2013.01); *G06F 19/3443* (2013.01); *G06F 19/3468* (2013.01); *A61M 15/00* (2013.01); *A61M 16/01* (2013.01); *A61M 2005/14208* (2013.01)

(58) Field of Classification Search
None
See application file for complete search history.

(56) References Cited

U.S. PATENT DOCUMENTS

| 5,533,957 A * | 7/1996 | Aldea .............................. 600/16 |
| 5,687,208 A | 11/1997 | Bae et al. |

(Continued)

FOREIGN PATENT DOCUMENTS

| DE | 101 60 270 | 6/2003 |
| DE | 103 45 836 | 4/2005 |

(Continued)

OTHER PUBLICATIONS

Definition of numerical modelling. The Dictionary of Physical Geography, 2000. Obtained online on Jul. 31, 2010 <<http://www.credoreference.com/entry/bkphsgeo/numerical_modelling>>.*

(Continued)

*Primary Examiner* — Russell S Negin
(74) *Attorney, Agent, or Firm* — Norris McLaughlin & Marcus, P.A.

(57) ABSTRACT

The invention relates to a method for the controlled dosage of a medicament as a function of time by means of a method for the determination of a corresponding dosage profile and corresponding control of a dosage instrument.

15 Claims, 10 Drawing Sheets

(51) Int. Cl.
  *G01N 31/00* (2006.01)
  *A61M 5/172* (2006.01)
  *G06F 19/26* (2011.01)
  *G06F 19/12* (2011.01)
  *A61M 15/00* (2006.01)
  *A61M 16/01* (2006.01)
  *A61M 5/142* (2006.01)

(56) References Cited

U.S. PATENT DOCUMENTS

| | | | | |
|---|---|---|---|---|
| 5,944,680 | A | * | 8/1999 | Christopherson et al. ...... 602/42 |
| 5,968,932 | A | * | 10/1999 | Winokur et al. ........... 514/227.8 |
| 8,038,645 | B2 | * | 10/2011 | Edginton et al. ................ 604/66 |
| 2003/0175350 | A1 | * | 9/2003 | Sugita et al. .................. 424/474 |
| 2005/0010193 | A1 | * | 1/2005 | Laurent et al. ................ 604/506 |

FOREIGN PATENT DOCUMENTS

| | | | |
|---|---|---|---|
| DE | 103 45 837 | | 4/2005 |
| WO | WO 00/01434 | * | 1/2000 |

OTHER PUBLICATIONS

Shahar et al. Sleep-disordered breathing and cardiovascular disease. Am J Respir Crit Care Med, 2001, vol. 163, pp. 19-25.*

Willmann et al. A physiologic model for simulating gastrointestinal flow and drug absorption in rats. Pharmaceutical Research. vol. 20, Nov. 2003, pp. 1766-1771.*

Sawamoto et al. Prediction of the plasma concentration profiles of orally administered drugs in rats on the basis of gastrointestinal transit kinetics and absorbability. J. Pharm. Pharmacol., 1997, vol. 49, pp. 450-457.*

Ostergaard et al. High resolution measurement of cerebral blood flow using intravascular tracer bolus passages. Part II: Experimental comparison and preliminary results, Magnetic Resonance in Medicine, vol. 36, 1996, pp. 726-736.*

Product Information—"Diprifusor™—Target Controlled Infusion (TCI) in anaestehetic practice"; AstraZeneca Anaesthesia, New Edition (1999), Alderley House, Alderley Park, UK.

Willmann, Stefan et al; "PK-Sim®: a physiologically based pharmacokinetic 'whole-body' model"; Biosilico vol. I, No. 4, (Sep. 2003) pp. 121-124, Elsevier Science Ltd.

Price, Paul S.; "Modeling interindividual variation in physiological factors used in PBPK models of humans"; Critical Reviews in Toxicology, 33(5); pp. 469-503 (2003) Taylor and Francis, Inc.

Ohnishi, A.; "A review of clinical use of theophylline in acute asthenia: factors influencing kinetic disposition and drug interactions"; Methods Find Exp. Clin Pharmacol 22(4); pp. 253-258, (2000) Prous Science.

Mitenko, Paul A, et al; "Pharmacokinetics of intravenous theophylline"; Clinical Pharmacology Therapeutics; 14, (1973) pp. 509-513, Montreal, Quebec, Canada.

Jameson, John P., et al; "Theophylline Pharmacokinetics in black Zimbabewean males", Therapeutic Drug Monitoring, 12, pp. 54-58 (1990) Ravene Press, Ltd. New York.

Gal, Peter et al; "Theophylline disposition in obesity"; Clin. Pharmacol. Ther (Apr. 1978), vol. 23, No. 4; The C.V. Mosby Co., pp. 438-444.

Jackson, S.H.D.; et al; "The relationship between theophylline clearance and age in adult life": Eur. J. Clin Pharmacol, Springer-Verlag (1989) 36: pp. 29-34.

Kato et al.; "Developmental changes of unbound theophylline"; Department of Pediatrics, Gifu University School of Medicine, 40 Tsukasa, Gifu 500 Japan.

Valenti, S.; "Bioavailability and pharmacokinetics of a new controlled-release theophylline preparation in the form of capsules containing Pellets"; Respiration 52; (1987) pp. 195-200.

Muller et al; "Theophylline kinetics in peripheral tissues in vivo in humans"; Naunyn-Schmiedeberg's Arch Pharmaol (1995) 352; pp. 438-441.

Meyer, Marvin c.; "Bioequivalence of immediate-release theophylline capsules"; Biopharmaceuticcs & Drug Disposition (1999) 20; pp. 417-419.

* cited by examiner

METHOD FOR THE TIMED DOSAGE OF MEDICAMENTS

This application is a 371 of PCT/EP2005/001745, filed Feb. 19, 2005, which claims foreign priority benefit under 35 U.S.C. §119 of the German Patent Application No. 10 2004 010 516.2 filed Mar. 4, 2004.

The invention relates to a method for the controlled dosage of a medicament as a function of time by means of a method for the determination of a corresponding dosage profile and corresponding control of a dosage instrument.

Computer-controlled infusion pumps, the delivery functions of which are determined by means of a pharmacokinetic model, are known according to the prior art by the keyword "TCI" (=Target Controlled Infusion) and are commercially available. The main application field of TCI is the control of intravenously administered narcotics (for example propofol, marketed as Diprifusor™ by AstraZeneca (Product information "Diprifusor™: Target Controlled Infusion (TCI) in anaesthetic practice", AstraZeneca Anaesthesia, New Edition (1998)). A disadvantage of these known methods is that the pharmacokinetic model is a three-compartment model fitted to experimental plasma data. With such a "black-box" method, there is no opportunity for the patient's individual physiological factors to be taken into account in the pharmacokinetic model. In contrast to this, physiology-based PK/PD models such as PK-Sim® developed by Bayer Technology Services GmbH (S. Willmann, J. Lippert, M. Sevestre, J. Solodenko, F. Fois, W. Schmitt: "PK-Sim®: a physiologically based pharmacokinetic 'whole-body' model", *Biosilico* 1, 121-124 (2003)), makes it possible to describe the influence of individual physiological and anatomical parameters such as organ size and composition, blood flow rates, etc. on the pharmacokinetic behavior of medicaments as a function of time (for example DE App. No. 10160270 and DE App. No. 10345836). These physiological and anatomical parameters can in turn be attributed to a few easily measurable quantities such as body weight and body mass index. DE App. No. 10345837 furthermore describes the way in which biochemical and genetic information, for example expression data of metabolically active enzymes or active transporters, can also be employed in order to determine a dose individually adapted to the patient. These systems are pure simulation models, however, which do not allow direct support of an application to the patient or clinical applications.

On the basis of said prior art, it is an object of the invention to develop an improved method which permits exact dosage of a medicament as a function of time while taking into account the patient's individual physiological, anatomical, biochemical and genetic factors.

The exact dosage of a medicament as a function of time is crucial for the safety and success of the treatment in many indication fields (for example anesthesia, diabetes, shock, sepsis, cardiovascular failure, asthma, cancer). With the aid of electronically controlled infusion pumps, medicaments can be administered with an arbitrarily predetermined time-variable rate. The resulting concentration-time profile and effect-time profile do not depend only on the dosage profile, however, but are essentially determined by the pharmacokinetic (PK) and pharmacodynamic (PD) properties of the substance in question. Physiology-based pharmacokinetic (PBPK) and pharmacodynamic computer models are in principle capable of simulating the concentration-time profile as well as the effect-time profile of a chemical substance in a patient's body, while taking into account individual physiological, anatomical, biochemical and genetic parameters.

The invention therefore relates to a method in which a PBPK/PD model is used in order to determine an optimal time profile of the dose for the individual patient by iterative adaptation either of the concentration-time profile, in the plasma or at the target site, or of the pharmacodynamic effect-time profile to a predetermined target time profile. The optimized time profile of the administration is then used as the input function for a dosage device. In combination with real-time measurements of physiological parameters, it is possible to set up a closed control loop that is far superior to the black-box methods known in the prior art, which do not utilize physiological knowledge.

It is particularly advantageous to combine the method with a real-time measurement of physiological parameters which may be subject to variations as a function of time, as is the case for example within the expression of metabolically active enzymes.

The essential feature of the invention consists in the combination of a physiology-based pharmacokinetic and/or pharmacodynamic (PBPK/PD) model with an automated dosage device, for example an electronically controlled infusion pump. PBPK/PD models are advantageous over non-physiological compartment models since they are capable of describing the effect of individual physiological, anatomical, biochemical and genetic factors on the pharmacokinetics and -dynamics in more detail.

By using the model PBK/PD, it is surprisingly now possible to determine very individual dosage rates adapted to the patient.

A schematic representation of the method according to the invention is shown in FIG. 1. The main component is a PBPK/PD model (101) which describes a particular type of body, particularly preferably that of a mammal, and requires a series of different parameters as input quantities:

1.) Substance-specific parameters of the medicament to be administered (102). Typical substance-specific parameters are e.g. physicochemical parameters such as lipophilicity, binding constants to human serum albumin and/or other plasma proteins, unbound plasma fraction, solubility in aqueous buffer solution or in intestinal fluid, size of the molecule (expressed by the molecular weight or molar volume), hepatic and/or renal clearance, permeability coefficients e.g. across artificial or biological membranes, and equilibrium distribution coefficients between plasma (or blood) and the various organs.

2.) Species-specific physiological, anatomical, biochemical and/or genetic input parameters, which are characteristic of the patient in question (103). These types of parameters include in particular body weight, volume components of individual organs with respect to the entire body volume, blood flow rates of individual organs, water, fat and lipid components of the individual organs, and parameters which characterize the expression and function of metabolically active enzymes (particularly in the liver and intestines) or the expression and function of proteins for the active transport of molecules through cell membranes. These parameters either may be directly measured or are correlated for particular populations with easily determinable patient parameters such as age, sex, body weight and lean body mass (P. S. Price, R. B. Conolly, C. F. Chaisson, E. A. Gross, J. S. Young, E. T. Mathis, D. R. Tedder: "Modeling interindividual variation in physiological factors used in PBPK models of humans", *Crit. Rev. Toxicol.* 33, 469-503 (2003)). Individual parameters or several parameters among these may be used in the method according to the invention.

3.) A dosage profile which describes the dose administered as a function of time (104).

The following is also specified:

4.) A target profile which indicates the intended concentration-time profile of the medicament to be administered in plasma, blood or directly at the biochemical target in the target organ or the intended effect-time profile ("SETPOINT profile", 105). This target profile is indication-specific and dependent on the medicament in question. In many clinically relevant cases, for example the administration of narcotics, a rectangular effect profile with maximally steep edges is desired, i.e. the intended effect (here narcosis) is to set in spontaneously then remain as constant as possible over a defined time period, and then drop off again rapidly at the end of the treatment. Either the time profile may be a simple function of time Z(t) or a tolerance range may alternatively or additionally be specified (defined as an interval between a maximum value and a minimum value $[Z_{min}(t) \ldots Z_{max}(t)]$).

On the basis of a start function to be selected expediently for the dosage profile, the PBPK/PD model calculates the individual concentration-time profile or effect-time profile for the substance in question with the aid of the information from 1.)-2.) ("ACTUAL profile", 106). Here, fundamentally different routes for the administration of the medicament may be envisaged in the PBPK/PD model. The medicament may be administered intravenously, intra-arterially, intraperitoneally, intramuscularly, subcutaneously, topically, orally or inhalatively via the upper airways and/or the lungs. Intravenous application is particularly important and preferred.

The next step of the method consists of an iterative optimization process, in which the dosage profile is varied until the simulated concentration-time profile or effect-time profile matches the SETPOINT profile (107, 108). As a result of this numerical optimization, the dosage time profile is obtained which causes the desired concentration-time or effect-time profile for the relevant substance in the individual patient, or exhibits the least deviation therefrom. Gradient methods, gradient-free methods, stochastic methods or evolutionary methods may be envisaged as numerical optimization methods. Among gradient methods, the quasi-Newton or Newton methods are particularly preferred, and in particular the nested interval method among gradient-free methods. The Monte-Carlo method is preferred in particular among stochastic methods, and the method of genetic optimization represents a particularly preferred form of an evolutionary method.

This dosage profile is employed in the last step in order to control an automatic dosage device.

Accordingly, the present invention also relates to a method for the controlled dosage of a medicament as a function of time, consisting of the following steps:

a) Specification of an indication- and substance-dependent target profile, which indicates a desired concentration-time profile or a desired effect-time profile, b) Physiology-based pharmacokinetic and/or pharmacodynamic simulation with a time-variable application profile while taking into account individual anatomical, physiological and/or genetic parameters of the body to be treated and substance-specific input parameters of the medicament to be administered, c) Iterative numerical adaptation of the application profile until the simulated time profile matches the predetermined target profile, or shows the maximum achievable match therewith, d) Control of a dosage device on the basis of the result in c).

The method according to the invention is particularly advantageous when physiological parameters, which have an effect on the pharmacokinetic or pharmacodynamic behavior of the medicaments, are time-variable. Examples of physiological parameters which can change during the therapy method are the blood flows of the gastrointestinal tract and the liver, which are influenced and modified inter alia by the absorption of nutrients, or (over a longer timescale) the expression rates of transporters or metabolically active enzymes. If such parameters are measured in a real-time during the therapy, then their time-varying effect can also be taken into account in the optimization of the dosage profile by the method according to the invention.

In certain cases, for example anesthesia, it may be expedient to not only regulate the dosage device by the desired pharmacokinetic or pharmacodynamic target profile, but also to employ an external measurement quantity as a further input parameter.

In a particular embodiment, the success of the therapy is additionally monitored online by one or more suitable measurement probes, which measure for example the depth of narcosis in anesthesia, and the measurement signals are integrated as additional input quantities in the method. The control of the dosage device is then not purely regulated by the pharmacodynamic or pharmacokinetic target profile, but also incorporates external measurement signals. For example, the supply of a narcotic may be increased when the measured depth of narcosis falls below a critical value. In this way, it is possible to set up a closed control loop which optimizes the time dosage of the medicament by incorporating online measurement values and physiological simulations in real-time. In this embodiment, the response of the pharmacodynamic or pharmacokinetic profile to changes in the application rate, which is known from the physiological simulation, is used in order to readapt the rate of the medicament supply to the patient's requirements as indicated by the measurement probe. In another particular embodiment, only the measurement probe signal is employed temporarily for the regulation if there is a critical situation (for example if the patient is about to wake early from the narcosis).

All methods based on said parameters are in principle suitable as simulation methods, the methods claimed in DE App. No. 10160270 and DE App. No. 10345836 being particularly suitable and preferred according to the invention.

Besides the application of the method according to the invention as an aid for carrying out a medical therapy, the method according to the invention may also be used as an aid directly in clinical trials or animal trials, for example in order to start off the runs with clinically "expedient" doses and to minimize the typical "settling in" of the doses, i.e. the empirical-iterative arrival at excessive or insufficient doses which alternatingly approach the optimum, and therefore minimize the burden on the bodies being treated and maximize the likelihood of the experiment's success.

Humans and animals are therefore suitable as a target group for the application of the method according to the invention, especially humans and economically useful, breeding, laboratory, test and pet animals. The method is more particularly preferably used as an aid for the therapeutic treatment of humans or clinical trials on humans.

Economically useful and breeding animals include mammals, for example cows, horses, sheep, pigs, goats, camels, water buffalo, donkeys, rabbits, fallow deer, reindeer, animals prized for fur, for example mink, chinchillas, raccoons, birds, for example chickens, geese, turkeys, ducks, pigeons, and bird species kept at home and in zoos.

Laboratory and test animals include mice, rats, guinea pigs, hamsters, rabbits, dogs, cats, pigs and apes, respectively in all species, subspecies and breeds.

Pet animals include dogs and cats.

Electronically controlled infusion pumps, inhalers or electronically controlled release capsules for oral application may be envisaged as the electronically controlled dosage device. Electronically controlled infusion pumps are particularly suitable.

The method according to the invention is particularly advantageous for those indications and active agents which have only a narrow "therapeutic window". A narrow therapeutic window means that there is only a small concentration range in which the desired pharmacological effects do actually occur but at the same time no undesired side-effects are to be observed. Examples of indication fields with narrow therapeutic windows are all types of cancer diseases, infectious diseases, in particular bacterial and viral infections, cardiovascular diseases, in particular high blood pressure, lipidemia, angina pectoris and myocardial infarction, diseases of the central nervous system such as Alzheimer's disease, schizophrenia, epilepsy, chronic headaches (migraines), analgesia and anesthesia, psychiatric diseases, in particular depression and anxiety, metabolic diseases, for example diabetes and impairments of fat metabolism (obesity), respiratory diseases such as asthma and bronchitis, immune diseases, in particular allergies, rheumatism and multiple sclerosis, diseases of the gastrointestinal tract, in particular ulcers of the stomach and duodenum and Crohn's disease, as well as vascular diseases, in particular those which cause erectile dysfunction, and states of acute shock.

EXAMPLE

The invention will be explained in more detail below with the aid of an example; this example illustrates the present invention but is in no way to be regarded as a limitation.

The example is based on simulations with the physiology-based pharmacokinetic model PK-Sim® developed by Bayer Technology Services.

Theophylline, a medicament for asthma therapy, was selected as an example substance. The peculiarity of this substance is that it has only a very narrow concentration range in which the substance is therapeutically effective. This so-called "therapeutic window" is described in the literature as being 5-10 to 20 mg/l (plasma concentration) (A. Ohnishi: "A Review of Clinical Use of Theophylline in Acute Asthma: Factors Influencing Kinetic Disposition and Drug Interactions", *Methods Find. Exp. Clin. Pharmacol.* 22, 253-258 (2000)). A sufficient anti-asthmatic effect is not generally achieved at plasma concentrations below 5 mg/l, and the risk of undesired side-effects such as nausea, trembling and accelerated heart rate increases above a plasma concentration of 20 mg/l (A. Ohnishi: "A Review of Clinical Use of Theophylline in Acute Asthma: Factors Influencing Kinetic Disposition and Drug Interactions", *Methods Find. Exp. Clin. Pharmacol.* 22, 253-258 (2000)). An added difficulty in the therapeutic use of theophylline is the known fact that the pharmacokinetics of this medicament depend strongly on the patient's individual factors, for example age, sex or body fat level. Particularly the metabolization rate (P. A. Mitenko, R. I. Ogilvie: "Pharmacokinetics of intravenous Theophylline", Clin. Pharm. Therap. 14, 509-513 (1973); J. P. Jameson, A. Munyika: "Theophylline Pharmacokinetics in Black Zimbabwean Males", Therap. Drug Monitoring 12, 54-58 (1990); P. Gal, W. J. Jusko, A. M. Yurchak, B. A. Franklin: "Theophylline disposition in obesity", Clin. Pharmacol. Ther. 23, 438-44 (1978); S. H. D. Jackson, A. Johnston, R. Woollard, P. Turner: "The Relationship between Theophylline Clearance and Age in Adult Life", Eur. J. Clin. Pharmacol. 36, 29-34 (1989)) and the free plasma fraction (Z. Trnavska: "Theophylline Protein Binding", Arzneim.-Forsch. 40, 166-170 (1990); Z. Kato, O. Fukutomi, N. Kondo: "Developmental Changes of unbound Theophylline", Ann Allergy Asthma Immunol. 80, 517 (1998)) are individually different and consequently lead to individually different plasma concentration profiles. In clinical use, this problem is tackled by experimentally monitoring the plasma concentration of theophylline (A. Ohnishi: "A Review of Clinical Use of Theophylline in Acute Asthma: Factors Influencing Kinetic Disposition and Drug Interactions", *Methods Find. Exp. Clin. Pharmacol.* 22, 253-258 (2000)). This method is comparatively elaborate, it requires repeated blood samples to be taken from the patient and is furthermore only expediently usable for long-term therapy with theophylline.

The way in which the problem of an optimal theophylline dose tailored individually to the patient can be resolved by the method according to the invention will be described below:

The following values for theophylline are used as substance-dependent input parameters (Table 1):

TABLE 1

| PARAMETER | VALUE |
|---|---|
| Lipophilicity (LogMA) | −0.2 |
| Free plasma fraction | 59% |
| Solubility | 2800 mg/l |
| Molar mass | 180 daltons |
| Intestinal permeability (only for taking orally, FIG. 2c) | $2.97 \times 10^{-6}$ cm/s |

The value of 59% used for the free plasma fraction represents an average value for an adult human (Z. Trnavska: "Theophylline Protein Binding", Arzneim.-Forsch. 40, 166-170 (1990); Z. Kato, O. Fukutomi, N. Kondo: "Developmental Changes of unbound Theophylline", Ann Allergy Asthma Immunol. 80, 517 (1998)). The following physiological and anatomical parameters were also assumed for the calculations with PK-Sim® (default parameters for humans, Table 2):

TABLE 2

| Organ/compartment | Volumes [ml] | Blood flow rates [ml/min] |
|---|---|---|
| Venous blood pool | 250 | –/– |
| Arterial blood pool | 140 | –/– |
| Lungs | 670 | 4670 |
| Stomach | 150 | 60 |
| Small intestine | 640 | 600 |
| Large intestine | 370 | 240 |
| Pancreas | 100 | 60 |
| Spleen | 180 | 180 |
| Liver | 1710 | 390 |
| Gall bladder | 20 | 0 |
| Kidneys | 720 | 1133 |
| Brain | 1486 | 700 |
| Heart | 330 | 240 |
| Muscle | 30200 | 550 |
| Bone | 12060 | 167 |
| Skin | 3020 | 50 |
| Fat | 10060 | 300 |
| Testicles | 35 | 2.6 |

It will first be shown that in principle it is possible to describe the plasma concentration-time profile of theophylline by PK-Sim® correctly on the basis of the aforementioned values. To this end, simulation results were compared with experimentally measured plasma concentration-time profiles (S. Valenti, P. Crimi, V. Brusasco: "Bioavailability and Pharmacokinetics of a New Controlled Release Theophylline Preparation in the Form of Capsules Containing Pellets", Respiration 52, 195-200 (1987); M. Müller, B. v. Osten, R. Schmid, E. Piegler, I. Gerngross, H. Buchegger, H. G. Eichler: "Theophylline kinetics in peripheral tissues in vivo in humans", Naunyn-Schmiedeberg's Arch. Pharmacol. 352, 438-441 (1995); M. C. Meyer, E. J. Jarvi, A. B. Straughn, F. R. Pelsor, R. L. Williams, V. P. Shah: "Bioequivalence of Immediate-release Theophylline Capsules", Biopharm. Drug Dispos. 20, 417-419 (1999)) and a muscle concentration-time profile from the literature (M. Müller, B. v. Osten, R. Schmid, E. Piegler, I. Gerngross, H. Buchegger, H. G. Eichler: "Theophylline kinetics in peripheral tissues in vivo in humans", *Naunyn-Schmiedeberg's Arch. Pharmacol.* 352, 438-441 (1995)) (FIG. 2). As can be seen in FIG. 2, the match of the simulated curves with the experimentally determined curves is very good.

Two virtual individuals will be considered below for the optimization of individual dosage profiles, who differ by way of example in respect of their total metabolization rate ("clearance"). Individual A has a total plasma clearance (CL) of 0.4 ml/min/kg, and individual B has 1.0 ml/min/kg. These values lie within the typical variation range of the plasma clearance of theophylline in humans (P. A. Mitenko, R. I. Ogilvie: "Pharmacokinetics of intravenous Theophylline", Clin. Pharm. Therap. 14, 509-513 (1973); J. P. Jameson, A. Munyika: "Theophylline Pharmacokinetics in Black Zimbabwean Males", Therap. Drug Monitoring 12, 54-58 (1990); P. Gal, W. J. Jusko, A. M. Yurchak, B. A. Franklin: "Theophylline disposition in obesity", Clin. Pharmacol. Ther. 23, 438-44 (1978); S. H. D. Jackson, A. Johnston, R. Woollard, P. Turner: "The Relationship between Theophylline Clearance and Age in Adult Life", Eur. J. Clin. Pharmacol. 36, 29-34 (1989)). The other relevant physiological and anatomical parameters, which are used in the following simulations, are assumed to be equal for both individuals and identical to the values collated in Table 2. At this point, it is naturally also conceivable to take into account a multiplicity of other individual differences, for example in free plasma fraction, body weight, fat level body or blood flow rate in one or more organs.

A plasma concentration of 15 mg/l is selected as the SETPOINT profile in this example, which is intended to be kept constant over a time period of 12 hours. The selected tolerance range is ±1 mg/l (represented in FIG. 3), i.e.

$$Z(t) = \begin{cases} 0, & t < 0 \\ 15 \text{ mg/L}, & 0 \le t \le 12 \text{ h} \\ 0, & t > 12 \text{ h} \end{cases} \text{ and} \quad (1)$$

$$Z_{min}(t) = \begin{cases} 0, & t < 0 \\ 14 \text{ mg/L}, & 0 \le t \le 12 \text{ h} \\ 0, & t > 12 \text{ h} \end{cases} \text{ and}$$

$$Z_{max}(t) = \begin{cases} 0, & t < 0 \\ 16 \text{ mg/L}, & 0 \le t \le 12 \text{ h} \\ 0, & t > 12 \text{ h}. \end{cases}$$

FIG. 4 shows the plasma concentration-time profiles simulated by PK-Sim® for the two individuals after a 1 mg/kg intravenous bolus administration of theophylline. The curves are used as a starting point for optimization of the dosage profile.

The infusion rate, i.e. the intravenously applied dose per time interval, is then varied iteratively in the next step. The increment of the dosage interval in this example is 0.1 hour=6 minutes. This value is expediently to be selected so that it is adapted to the distribution and elimination kinetics of the substance.

The simulation result obtained (=ACTUAL profile) is then compared with the SETPOINT profile. In the case of a deviation of the ACTUAL profile from the SETPOINT profile which lies outside the valid tolerance range, the amount applied in the corresponding time step is varied until the ACTUAL profile matches the SETPOINT profile overall in the scope of the tolerance range. The optimization of the application profile was carried out by manual iteration in the present example. In the scope of a genuine therapy optimization, suitable numerical optimization methods are to be used at this point. Gradient methods, in particular quasi-Newton or Newton methods, as well as gradient-free methods such as nested intervals and stochastic methods such as Monte-Carlo methods may for example be envisaged here as suitable optimization methods.

A respective result of such a manual iterative optimization process is represented in FIGS. 5 (a) and (b). The dosage profiles associated with these ACTUAL profiles are shown in FIGS. 6 (a) and (b). These dosage profiles determined in this way are used in the last step of the method as an input function for the control of a conventional dosage machine, for example an electronically controlled infusion pump.

Figure 1:
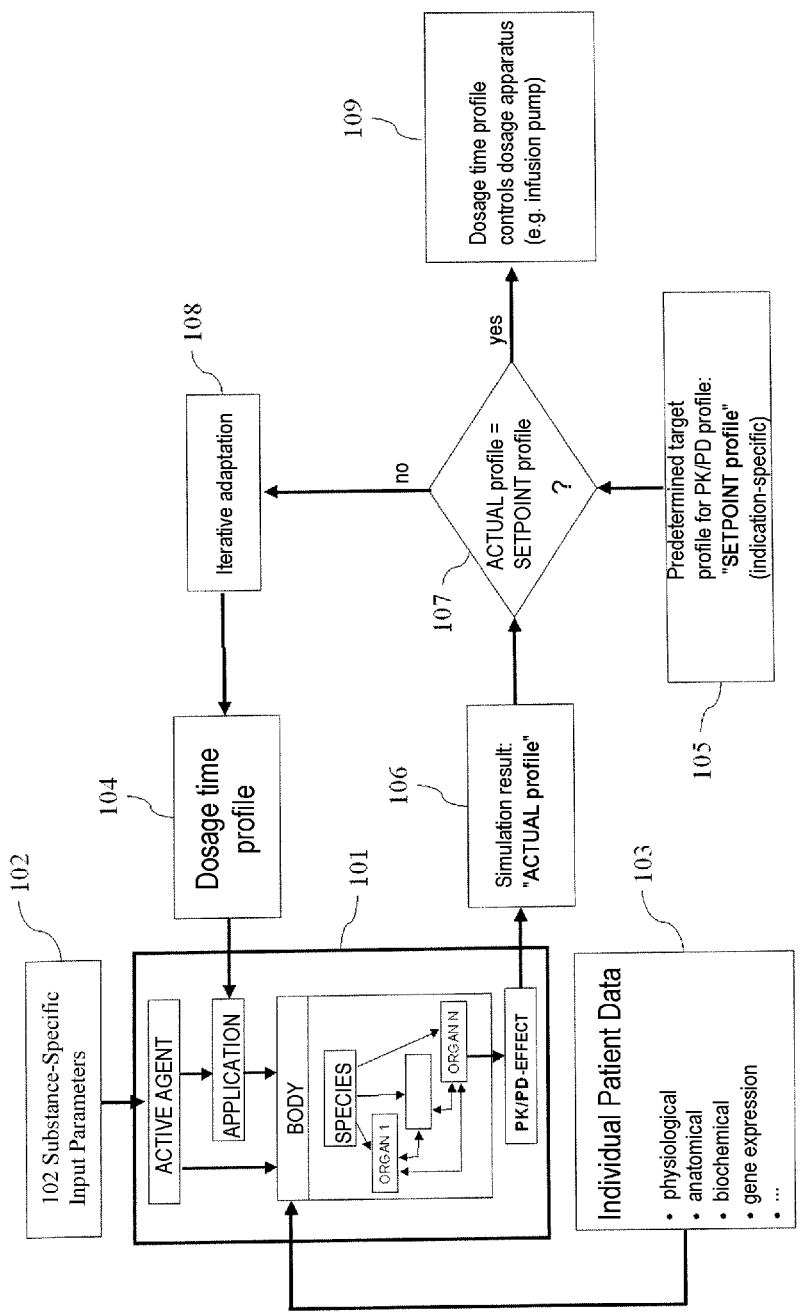
FIG. 1: Schematic representation of the method for the timed dosage medicaments.
Figure 2:
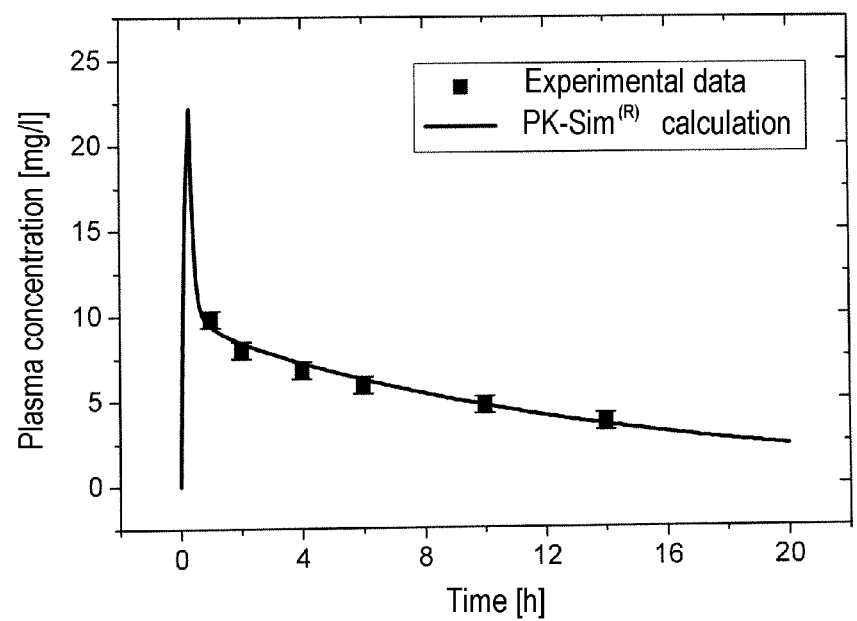
FIG. 2: Comparison between experimental concentration-time profiles of theophylline from the literature with simulation results by PK-Sim® with metabolization rates adapted to the respective experimental data:
a) Intravenous infusion of 5.58 mg/kg over 20 minutes. The plasma clearance here is CL=0.40 ml/min/kg. (source: [12])
b) Intravenous infusion of 240 mg over 10 minutes. The plasma clearance here is CL=0.25 ml/min/kg. (source: [13])
c) Peroral administration of 200 mg of an immediately releasing formulation (mean and standard deviation of three bioequivalent immediate release capsules [14]). The plasma clearance here is CL=0.50 ml/min/kg.
Figure 2:
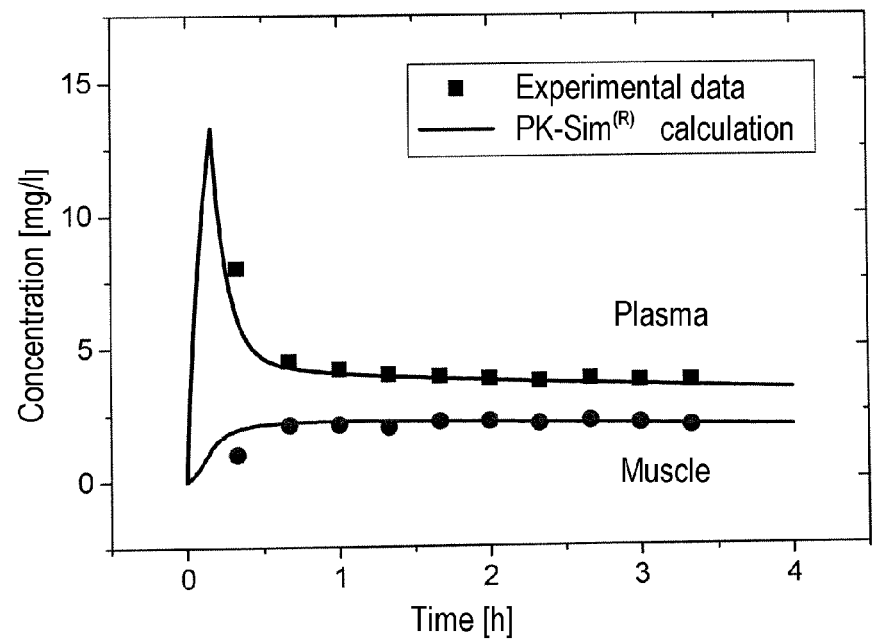
Figure 2:
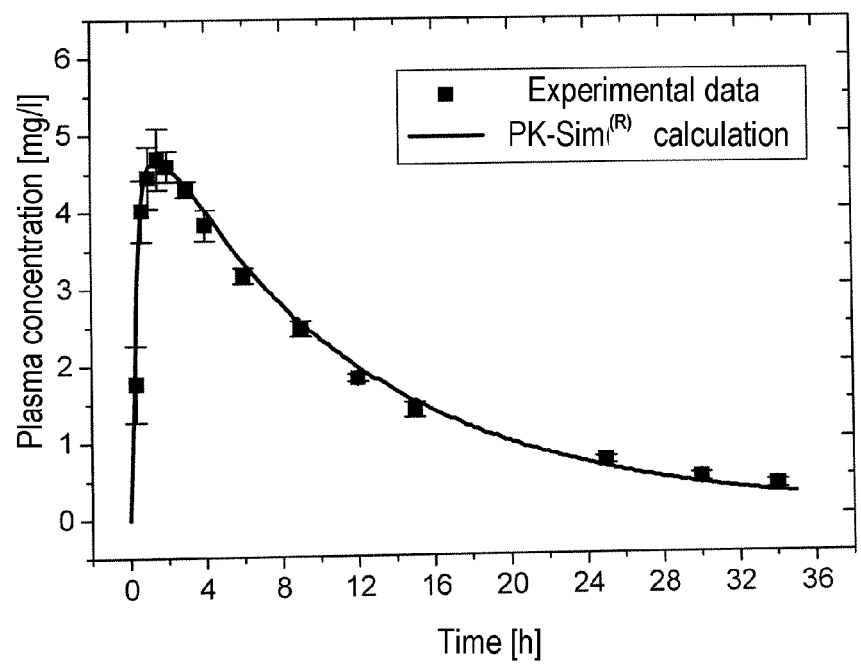
Figure 3:
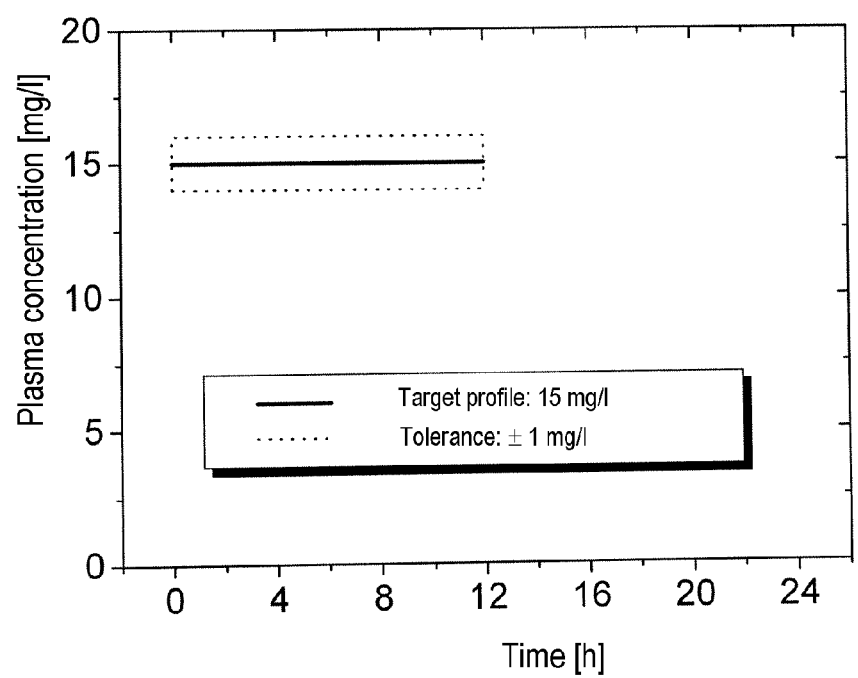
FIG. 3: Specification of the target profile (=SETPOINT profile)
Figure 4:
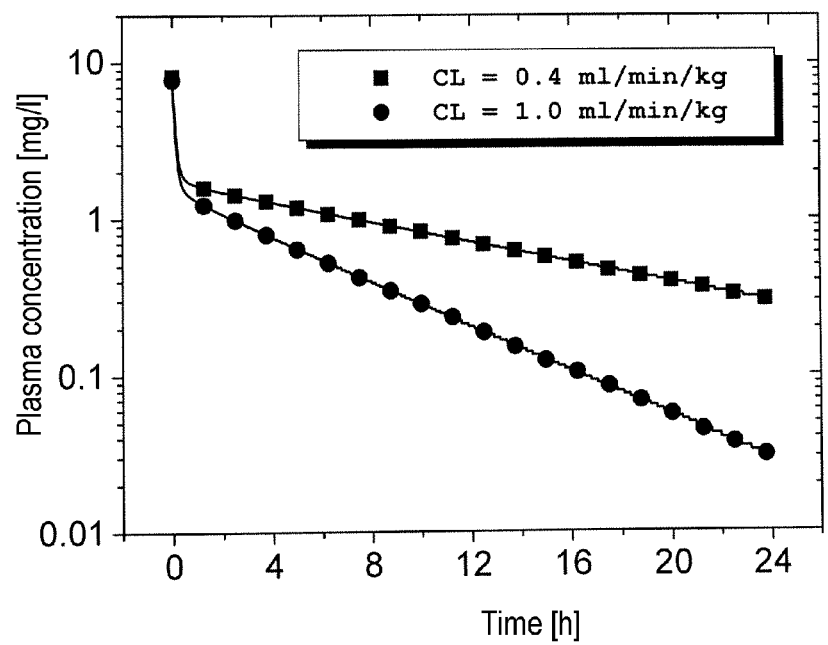
FIG. 4: Simulation result for the intravenous bolus administration of 1 mg/kg theophylline in individuals A (CL=0.4 ml/min/kg) and B (CL=1.0 ml/min/kg).
Figure 5:
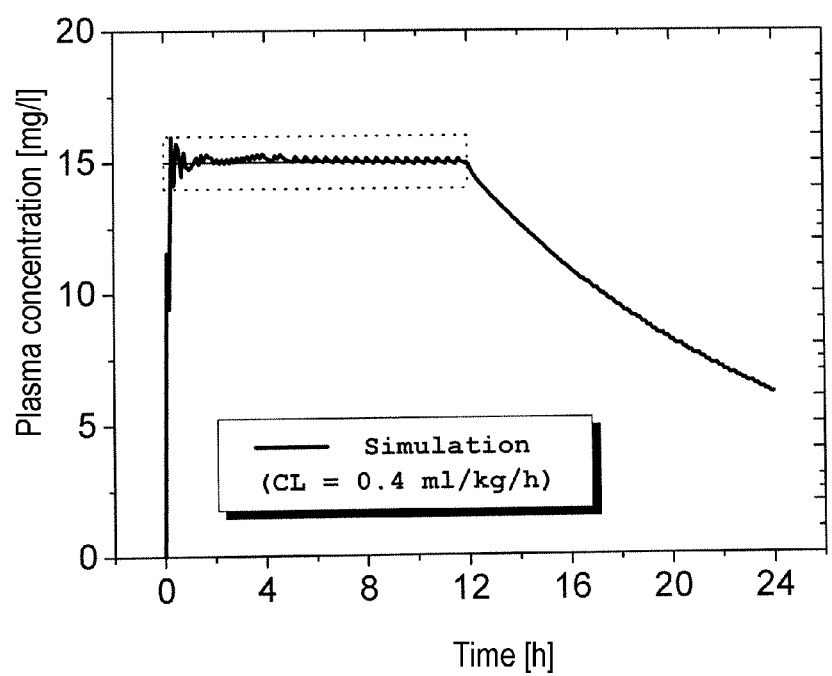
FIG. 5: Simulated plasma concentration-time profile (ACTUAL profile) after iterative adaptation of the dosage profile for individuals A (a) and B (b).
Figure 5:
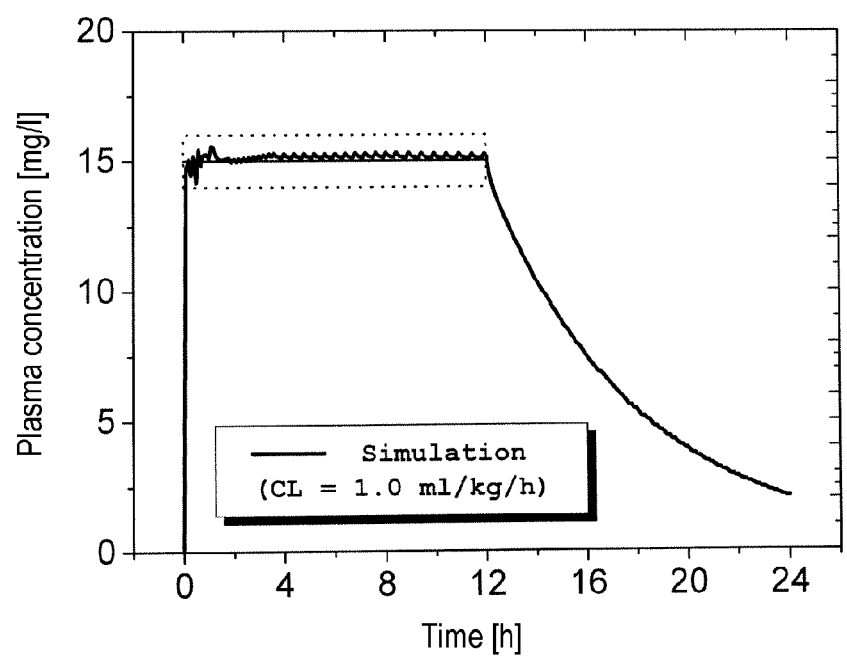
Figure 6:
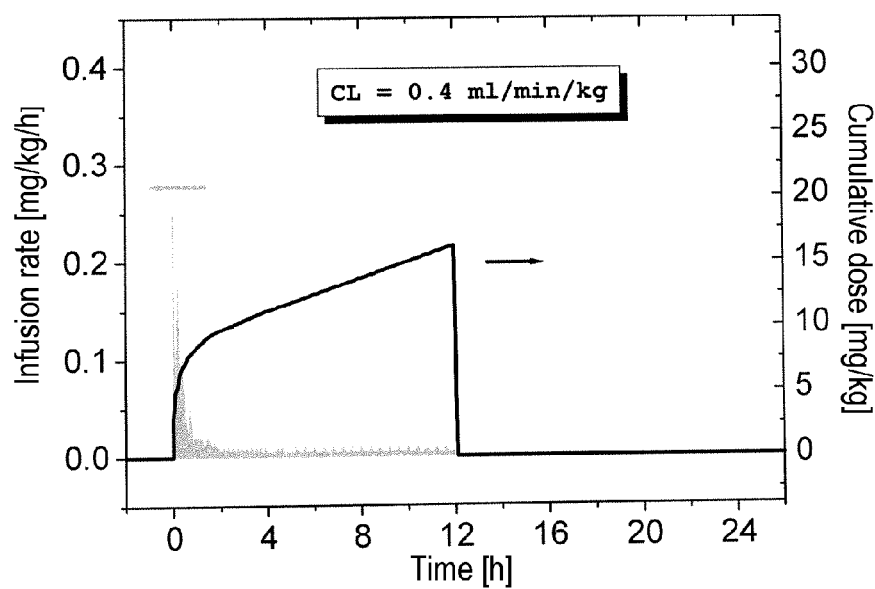
FIG. 6: Optimized dosage profile for individuals A (a) and B (b).
Figure 6:
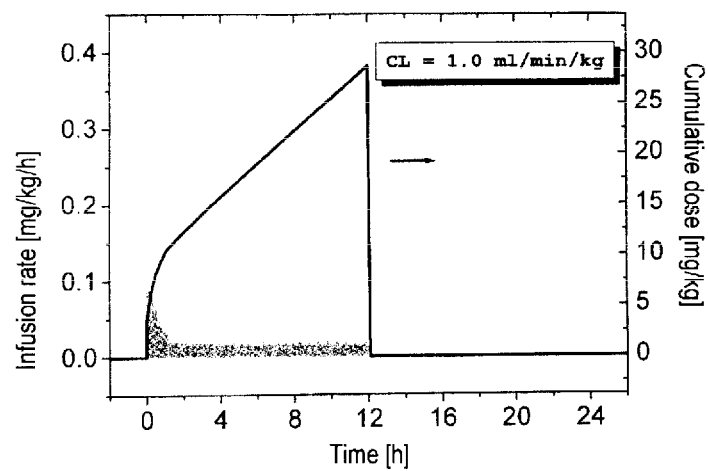

The invention claimed is:

1. A method of administering a medicament having a narrow therapeutic window into a body of a patient in need of treatment with said medicament as a function of time with the aid of a computer-controlled dosage device, said method comprising the following steps:
   a) inputting an indication- and substance-dependent predetermined target profile, which indicates a desired concentration-time profile or a desired effect-time profile and a dosage time profile which describes the dose administered as a function of time into a physiology-based and/or pharmacodynamic computer model module, b) physiology-based pharmacokinetic and/or pharmacodynamic simulating with a time-variable application profile while taking into account individual anatomical, physiological and/or genetic parameters of the body to be treated and substance-specific input parameters of the medicament to be administered within the physiology-based and/or pharmacodynamic computer model module and outputting a simulated time profile, c) iterative numerical adapting of the dosage time profile until the simulated time profile matches the predetermined target profile to yield an adapted dosage time profile, and d) outputting of the adapted dosage time profile of c) to control the dosage device according to the adapted dosage time profile, and administering said medicament having said narrow therapeutic window to said patient using said dosage device controlled by said adapted dosage time profile.

2. The method as claimed in claim 1, wherein the administering of the medicament is to a human or an animal.

3. The method as claimed in claim 1, wherein the administering is by an application route selected from the group consisting of intravenous application, intra-arterial application, intraperitoneal application, intramuscular application, subcutaneous application, topical application, oral application and inhalative application.

4. The method as claimed in claim 3, wherein the administering is by an application route selected from the group consisting of intravenous application, intra-arterial application, intraperitoneal application, intramuscular application, subcutaneous application, topical application and oral application.

5. The method as claimed in claim 1, wherein the patient's individual parameters to be taken into account are selected from the group consisting of blood flow rates, volumes and composition of individual organs, gene expression data of metabolically active enzymes or active transporters.

6. The method as claimed in claim 5, wherein one or more of the anatomical, physiological and/or genetic parameters is optionally time-variable.

7. The method as claimed in claim 5, wherein one or more of the anatomical, physiological and/or genetic parameters are measured in real-time during the application and integrated as additional input quantities into the physiology-based and/or pharmacodynamic computer model module.

8. The method as claimed in claim 1, wherein the substance-specific parameters to be taken into account are selected from the group consisting of lipophilicity, binding constants to plasma proteins, free fraction in plasma, solubility, permeability coefficient, molar mass, molar volume, and organ/plasma or organ/blood distribution coefficient.

9. The method as claimed in claim 1, wherein a numerical optimization method is used that is selected from the group consisting of: gradient methods; gradient-free methods; and stochastic methods.

10. The method as claimed in claim 1, wherein the dosage device is an electronically controlled infusion pump, an inhaler or an electronically controlled release capsule for oral application.

11. The method as claimed in claim 1, wherein success of said administering is additionally monitored online by one or more suitable measurement probes and their measurement signal or measurement signals are co-employed in order to control the dosage device.

12. The method according to claim 1, wherein the administering is for treatment of a disease or disorder selected from the group consisting of cancer diseases, infectious diseases, cardiovascular diseases, diseases of the central nervous system, psychiatric diseases, respiratory diseases, immune diseases, diseases of the gastrointestinal tract, vascular diseases and states of acute shock.

13. The method according to claim 12, wherein the disease or disorder is selected from the group consisting of bacterial infections, viral infections, high blood pressure, lipidemia, angina pectoris, myocardial infarction, Alzheimer's disease, schizophrenia, epilepsy, chronic headaches (migraines), analgesia, anesthesia, depression, anxiety, diabetes, impairments of fat metabolism (obesity), asthma, bronchitis, allergies, rheumatism, multiple sclerosis, ulcers of the stomach and duodenum, Crohn's disease, and erectile dysfunction.

14. A method of intravenously administering a medicament having a narrow therapeutic window into a body of a patient in need of treatment with said medicament as a function of time with the aid of a computer-controlled dosage device, said method comprising the following steps:

a) inputting an indication- and substance-dependent predetermined target profile, which indicates a desired concentration-time profile or a desired effect-time profile and a dosage time profile which describes the dose administered as a function of time into a physiology-based and/or pharmacodynamic computer model module, b) physiology-based pharmacokinetic and/or pharmacodynamic simulating with a time-variable application profile while taking into account individual anatomical, physiological and/or genetic parameters of the body to be treated and substance-specific input parameters of the medicament to be administered within the physiology-based and/or pharmacodynamic computer model module and outputting a simulated time profile, c) iterative numerical adapting of the dosage time profile until the simulated time profile matches the predetermined target profile to yield an adapted dosage time profile, and d) outputting of the adapted dosage time profile of c) to control the dosage device according to the adapted dosage time profile, and intravenously administering said medicament having said narrow therapeutic window to said patient using said dosage device controlled by said adapted dosage time profile.

15. A method of administering a medicament into a body of a patient in need of treatment with said medicament as a function of time with the aid of a computer-controlled dosage device, said method comprising the following steps:

a) inputting an indication- and substance-dependent predetermined target profile, which indicates a desired concentration-time profile or a desired effect-time profile and a dosage time profile which describes the dose administered as a function of time into a physiology-based and/or pharmacodynamic computer model module, b) physiology-based pharmacokinetic and/or pharmacodynamic simulating with a time-variable application profile while taking into account individual anatomical, physiological and/or genetic parameters of the body to be treated and substance-specific input parameters of the medicament to be administered within the physiology-based and/or pharmacodynamic computer model module and outputting a simulated time profile, c) iterative numerical adapting of the dosage time profile until the simulated time profile matches the predetermined target profile to yield an adapted dosage time profile, and
d) outputting of the adapted dosage time profile of c) to control the dosage device according to the adapted dosage time profile, and administering said medicament having said narrow therapeutic window to said patient using said dosage device controlled by said adapted dosage time profile.

* * * * *